United States Patent [19]

Petit et al.

[11] Patent Number: 5,728,661
[45] Date of Patent: Mar. 17, 1998

[54] (2,3-DIHYDROXYPROPYL 2-(1-OXOALKYL) AMINO-2-DEOXYGLUCOPYRANOSIDES, A PROCESS FOR THEIR PREPARATION AND THEIR USES

[75] Inventors: Serge Petit, Cusy; Daniel Bernard, Courbevoie; Henri-Jean Caupin, Versailles, all of France

[73] Assignees: Elf Atochem, S.A.; Ceca S.A., both of Puteaux, France

[21] Appl. No.: 731,926

[22] Filed: Oct. 21, 1996

[30] Foreign Application Priority Data

Oct. 18, 1995 [FR] France .................... 95 12215

[51] Int. Cl.$^6$ .................................... A61K 7/045
[52] U.S. Cl. .................. 510/126; 536/55.2; 510/130; 510/433; 510/470; 510/502; 424/DIG. 4
[58] Field of Search .................. 574/62; 536/55.2, 536/17.2; 510/130, 433, 470, 502, 126

[56] References Cited

U.S. PATENT DOCUMENTS

| | | | |
|---|---|---|---|
| 5,057,605 | 10/1991 | Yoshimura et al. | 536/4.1 |
| 5,077,039 | 12/1991 | Baur et al. | 424/70 |
| 5,223,179 | 6/1993 | Connor et al. | 252/548 |
| 5,338,487 | 8/1994 | Connor et al. | 252/357 |

FOREIGN PATENT DOCUMENTS

| | | |
|---|---|---|
| 2095800 | 11/1993 | Canada . |
| A-0569682 | 11/1996 | European Pat. Off. . |

OTHER PUBLICATIONS

French Search Report dated Jun. 4, 1996.

*Primary Examiner*—Ardith Hertzog
*Assistant Examiner*—John R. Hardee
*Attorney, Agent, or Firm*—Millen, White, Zelano, & Branigan, P.C.

[57] ABSTRACT

The subject of the invention is the compounds of formula:

$$\begin{array}{c}\text{compound (I)}\end{array}$$

in which R denotes a saturated or unsaturated, linear or branched alkyl group containing from 5 to 21 carbon atoms.

The invention also relates to a process for the preparation of the abovementioned compounds, characterized in that it consists in a) forming an N-acylglucosamine from glucosamine hydrochloride and $C_6$–$C_{22}$ acid chloride, and b) reacting the compound from stage a) with glycerol in the presence of an acid catalyst.

It also relates to detergent or cosmetic compositions including the abovementioned compounds.

16 Claims, No Drawings

(2,3-DIHYDROXYPROPYL 2-(1-OXOALKYL) AMINO-2-DEOXYGLUCOPYRANOSIDES, A PROCESS FOR THEIR PREPARATION AND THEIR USES

FIELD OF THE INVENTION

The present invention relates to the field of surface-active agents of neutral character. It relates more particularly to 2,3-dihydroxypropyl 2-(1-oxoalkyl)amino-2-deoxyglucopyranosides, to the process for their preparation, the compositions containing the said compounds and to their uses.

BACKGROUND OF THE INVENTION

In the field of surface-active agents there is a continuous search for compounds devoid of toxic and irritant character, especially vis-à-vis the skin and the mucosae of the user with which they come into contact, it being additionally necessary for such compounds not to harm the environment.

Surface-active agents find applications in sectors as diverse as cosmetology, hair care and detergency in an industrial environment. They are generally used in the form of compositions which, apart from their main function, must henceforth exhibit an ever-increasing number of specific properties.

A shampoo, for example, is no longer sought after merely for its detergent properties, but also for its antidandruff activity, its ability to condition hair, to prevent itching and to impart a pleasant feel.

To obtain this objective a first option consists in using one or several neutral surface-active agents in combination with agents exhibiting the required properties.

Neutral surface-active agents, which are generally polyoxyethylenated (B, Hefford, Surfactant Surveillance, S.P.C., pp. 35–36, Nov. 1991), and polyalkylglucosides derived from glucose (EP-A-569 682; P. A. Siracusa, Happi, pp. 100–108, April 1992; J. Thiem and T. Bocker, Special Publication of the Royal Society of Chemistry, vol. 107, pp. 123–147, 1992; P. Schulz, Chimica Oggi, pp. 33–38, August-September 1992; D. Balzer, Tenside, Surf. Der. vol. 28 No. 6, pp. 419–426, 1991; B. Salka, Cosmetics & Toiletries, Vol. 108, pp. 89–94, March 1993) have thus been proposed.

The abovementioned surface-active agents have in common a good detergency and low eye irritancy, the polyalkylglucosides being, furthermore, biodegradable.

However, their main disadvantage is that they are difficult to formulate because of their limited foamability and/or the large number of active agents in the composition.

Thus, such agents can be employed only in a small quantity because a washing and forming base consisting of an anionic surfactant has to be added to them. The irritant nature of the latter has to be tempered by the addition of an amphoteric third surface-active agent.

In addition, since polyoxyethylenated compounds are liable to contain 1,4-dioxane, which is suspected of having a carcinogenic action, it is probable that the degree to which they are incorporated will decrease in the future.

Polyalkylglucosides, for their part, are obtained in the form of mixtures resulting from inter- and/or intramolecular isomerization and oligomerization phenomena.

It follows that the formulation of compositions containing such surface-active agents is tricky.

A second option consists in limiting the number of active agents by the use of surface-active agents possessing specific properties.

Such agents have been described especially by Emmerling (Polym. Bull., vol. 6, pp. 305–308, 1982) and Inouye et al. (J. Am. Chem. Soc. vol. 78, pp. 2825–2832, 1956). They are compounds of the alkylglucosamine, especially N-acylglucosamine, type exhibiting specific properties such as protection against radiations (DE 2708667 and U.S. Pat. No. 4,323,561), the diagnosis and the transport of active agents via the formation of vesicles (WO 91/04013 and WO 88/06883), the treatment of allergies, acne or dermatitis (EP-A-209 770), immunostimulant activity (Vallani et al., Arzneim Forsch, vol. 39 No. 10, pp. 1190–1195, 1989), stimulation of hair growth (EP-A-348 184) and antimicrobial activity (J. Am. Oil Chemists' Soc., vol. 70 (1), pp. 17–22, 1993 and JP 03112905).

The major disadvantage of the abovementioned agents is their low solubility in water which, as a result, restricts their use. There is little hope of overcoming this disadvantage by converting them into chloride (J.A.O.C.S., vol 70(1), pp. 17–22, 1993 and JP61-57321) or into hydrobromide, because the irritant nature which characterizes most of the cationic surface-active agents is then introduced.

DESCRIPTION OF THE INVENTION

New neutral surface-active agents have now been found, characterized in that they correspond to the formula:

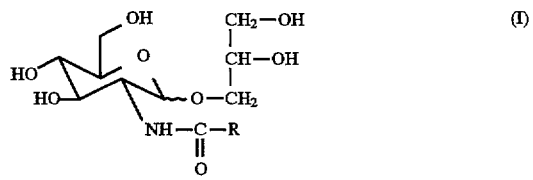

in which R denotes a saturated or unsaturated, linear or branched alkyl group containing from 5 to 21 carbon atoms.

The invention relates very particularly to the compounds of formula (I) in which the radical R contains from 7 to 17 carbon atoms and, still better, from 9 to 13.

In the present description the compounds of formula (I) are called 2,3-dihydroxypropyl 2-(1-oxoalkyl)amino-2-deoxyglucopyranosides.

The invention also relates to a process for the preparation of the compounds of formula (I), this process being characterized in that it consists in:

a) forming an N-acylglucosamine from glucosamine hydrochloride and $C_6$–$C_{22}$ acid chloride, and b) reacting the compound from stage a) with glycerol in the presence of an acid catalyst.

The glucosamine hydrochloride of the process according to the invention is generally obtained by the conventional methods for acidic hydrolysis of chitin.

The acid chloride of the process according to the invention is chosen from $C_6$–$C_{22}$ and preferably $C_8$–$C_{18}$ acid chlorides which have a saturated or unsaturated, linear or branched alkyl radical, with the exception of the chloride of undecylenic acid. This chloride may be prepared especially by reaction of the corresponding acid with thionyl chloride at a temperature of 60°–70° C. and distillation at reduced pressure of the acid chloride obtained.

The acid catalyst of the process according to the invention is chosen from the group consisting of acids in general, for example hydrochloric or sulphuric acid, an alkylsulphuric acid such as decyl- or laurylsulphuric acid, a sulphonic acid such as benzenesulphonic, para-toluenesulphonic or camphorsulphonic acid, an alkylsulphonic acid such as methanesulphonic, decylsulphonic, laurylsulphonic or sulphosuccinic acid, an alkyl sulphosuccinate such as decyl or lauryl sulphosuccinate, a perhalohydric acid such as perchloric acid, hypophosphorous acid or mixtures of these acids, and resins in $H^+$ form such as sulphonic resins and acidic clays. Sulphuric acid, methanesulphonic acid, succinic acid or an alkylsulphosuccinate, hypophosphorous acid and mixtures of these acids are preferably employed.

Stage a) of the process according to the invention consists in reacting the acid chloride and glucosamine hydrochloride in a molar ratio which is generally between 0.7 and 1.3 and preferably between 0.9 and 1.1.

In general, glucosamine hydrochloride is dissolved in aqueous sodium hydroxide at a concentration of between 6 and 60 g/liter and preferably 2.5 and 17.5 g/liter. The concentration of glucosamine hydrochloride in the solution is generally between 0.2 and 1 equivalent in mol/liter and preferably 0.285 and 0.5 equivalents in mol/liter.

The acid chloride and a solution of sodium hydroxide with a normality of between 1 and 10 and preferably 2 to 6 are added simultaneously to the glucosamine hydrochloride solution thus prepared.

The addition of acid chloride is generally performed at a flow rate of between 5 and 500 ml/hour and preferably 10 and 100 ml/hour.

The flow rate of the sodium hydroxide solution is adapted so that the pH of the reaction mixture is between 6 and 11 and preferably 8 and 10.5.

The temperature of the reaction mixture is generally between 0° and 80° C. and preferably 10° and 50° C.

The reaction mixture is advantageously kept stirred at between 50 and 800 revolutions/min and preferably 100 and 400 revolutions/min, especially with the aid of a twin-blade device.

After the addition of the acid chloride the reaction is allowed to continue in the abovementioned temperature and stirring conditions for a period that can vary from 0.25 to 24 hours and preferably from 0.5 to 6 hours.

At the end of the reaction the pH of the reaction mixture is adjusted to a value of between 4 and 8 and preferably 5 and 7 by addition of an acid in order to form a precipitate. It is obvious that any type of acid known to a person skilled in the art may be employed. Sulphuric acid, methanesulphonic acid, succinic acid, an alkyl sulphosuccinate, hypophosphorous acid and mixtures of these acids are advantageously employed.

The precipitate of the abovementioned reaction mixture can be recovered in two ways.

According to a first alternative form the precipitate is recovered by draining and continuous washing with water.

According to a second alternative form the precipitate is recovered by filtration of the reaction mixture, drained, washed 1 to 4 times, and preferably 2 to 3 times, with 0.1 to 2 liters and preferably 0.2 to 1 liter of water; and drained again.

The precipitate obtained at the end of stage a) consists of N-acylglucosamine.

In stage b) of the process according to the invention the abovementioned N-acylglucosamine precipitate is reacted with glycerol in the presence of an acid catalyst.

Glycerol is generally used in the process so that the ratio of the number of molar equivalents of glycerol to the number of molar equivalents of N-acylglucosamine is between 1 and 50 and preferably 5 and 30.

In general, when the acid catalyst as defined above is an acid, the ratio of the number of molar equivalents of the acid to the number of molar equivalents of N-acylglucosamine is between $10^{-3}$ and 1 and preferably $10^{-2}$ and $10^{-1}$. When this catalyst is a resin or a clay, the quantity employed, expressed as weight equivalent calculated on the basis of 1 molar equivalent of N-acylglucosamine, is between 0.05 and 6.

When a alehydrating effect is sought, a conventional dehydrating agent such as a molecular sieve or a zeolite may be optionally added to the reaction mixture.

The reaction is generally performed at a pressure of between 0.13 and 101.32 kPa, preferably 0.013 and 39.99 kPa, at a temperature of between 25° and 200° C., preferably 80° and 105° C., and for a period that can vary from 0.25 to 24 hours, preferably 1 to 12 hours.

At the end of the reaction the catalyst is removed by filtration. When it is an acid, it is firstly converted into a salt of the corresponding acid, for example by the addition of a sodium hydrogencarbonate solution.

For the purpose of facilitating the filtration stage it is optionally possible to employ a solvent chosen from ethers, for example tetrahydrofuran, ethylene glycol dimethyl ether, halogenated hydrocarbons, for example dichloromethane, dichloroethane and chloroform, esters, for example ethyl acetate, propyl acetate and butyl acetate, alcohols, for example methanol, ethanol and propanol, solvents of the amide type, for example N-methylformamide and N,N-dimethylformamide, and mixtures of these solvents. An alcohol is preferably employed.

The reaction mixture thus obtained is a solution of 2,3-dihydroxypropyl 2-(1-oxoalkyl)amino-2-deoxyglucoparanoside in glycerol, which is generally in the form of a mixture of the $\alpha$ and $\beta$ anomers in position 1, the proportion of the $\alpha$ anomer relative to the $\beta$ anomer being preferably between 80/20 and 90/10. The $\alpha$ and $\beta$ anomers may be optionally separated, for example by chromatography on a silica column.

The 2,3-dihydroxypropyl 2-(1-oxoalkyl)amino-2-deoxyglucopyranoside according to the invention has excellent forming, wetting, dispersing, emulsifying and solubilizing properties and, in addition, has an antidandruff activity, the ability to soften and to tone up the skin, and the possibility of forming vesicles for the stabilization and transport of active principles.

The compounds according to the invention are particularly recommended for preparing detergent compositions, which are especially intended for the industrial environment, or cosmetic ones. These compositions, which also form a subject of the present invention, may contain only one of the compounds of formula (I) or a mixture of the said compounds.

The detergent compositions according to the invention are characterized in that they contain from 0.1 to 60% and preferably 10 to 40% by weight of 2,3-dihydroxypropyl 2-(1-oxoalkyl)amino-2-deoxyglucopyranoside and from 40 to 99.9% and preferably 60 to 90% by weight of a detergent base and/or of an adjuvant.

The detergent base is generally chosen from anionic, nonionic, cationic or amphoteric surfactants and mixtures of these compounds.

The adjuvant is generally chosen from the adjuvants or mixtures of adjuvants which are known in the field of washing liquids or powders, especially zeolites and complexants for calcium and magnesium.

The cosmetic compositions which are the subject of the invention are characterized in that they contain from 0.1 to 50% and preferably 5 to 35% by weight of 2,3-dihydroxypropyl 2-(1-oxoalkyl)amino-2-deoxyglucopyranoside and from 50 to 99.9% and preferably 65 to 95% by weight of an excipient and/or a detergent base and/or an adjuvant.

The cosmetic compositions may be in the form of mild liquid soap, shampoo, foam bath, shower gel or a care formula, especially an ointment, cream and beauty milk.

When the composition is a mild liquid soap it contains from 5 to 30% by weight, and preferably from 5 to 20%, of 2,3-dihydroxypropyl 2-(1-oxoalkyl)amino-2-deoxyglucopyranoside and 70 to 95% and preferably 80 to 95% by weight of an excipient.

The excipient is generally chosen from anionic surfactants such as sodium cocoyl isethionate, sodium lauryl sulphate or the sodium salt of an alkyl peptide, amphoteric surfactants such as alkylamidopropylbetaine, and in particular cocoamidopropylbetaine, heavy mineral oils, cellulose derivatives such as carboxymethyl cellulose, solvents such as alcohols and more particularly ethanol or propylene glycol, complexants such as EDTA, sodium chloride, fatty alcohols such as cetyl alcohol, preserving agents, perfumes, dyes and mixtures of these compounds.

When the composition according to the invention is a shampoo, especially a mild shampoo for frequent use, a mild antidandruff shampoo, a treating shampoo or one with a hair-conditioning effect, it preferably contains from 5 to 35% by weight of a detergent base containing from 10 to 75% by weight of 2,3-dihydroxypropyl 2-(1-oxoalkyl)amino-2-deoxyglucopyranoside and from 65 to 95% by weight of an adjuvant.

The detergent base is generally chosen from alkyl ether sulphates such as sodium or magnesium lauryl ethyl sulphate, polyoxyethylenated alkyl ether sulphates such as polyoxyethylenated sodium lauryl ether sulphate, alkylbetaines such as cocoylbetaine, alkylamidopropylbetaines such as cocoylamidopropylbetaine, an alkyldimethylaminoacetic acid betaine such as lauryldimethylaminoacetic acid. betaine, alkyldimethylaminohydroxypropyl sulphobetaine, sodium α-oleinsulphonates, alkyl polyethylene glycols such as octadecyl PEG 15, alkyl imidazoliumbetaines such as cocoylimidazoliumbetaine, alkyl ether sulphosuccinates such as disodium lauryl ether sulphosuccinate, β-alkylaminopropionates such as sodium β-laurylaminopropionate, alkyldiaminoethylglycines such as sodium laurylalkyldiaminoethylglycine and mixtures of these compounds.

The adjuvant is generally chosen from thickeners, texturizing agents such as fatty acid diethanolamides, more particularly cocoyldiethanolamide, and alkyl acrylates, more particularly lauryl acrylate, sodium chloride, ethylene glycol dialkylcarboxylates, more particularly ethylene glycol distearate, fatty amine oxides, more particularly N-cocoyl oxide, which compounds are generally employed in a proportion of 0–10% by weight.

The adjuvant may also be chosen from conditioning agents, emollients such as wheat protein hydrolysates and cellulose ethers containing quaternary ammoniums (nitrogen content: 1–3%, MW: 50-150 000), acrylamide/dimethylalkylammonium chloride copolymers (0.5–5% by weight), complexants such as EDTA and galactaric acid (0.1–1% by weight), perfumes, pearlescent agents, preserving agents, acidifying agents, water and mixtures of these compounds.

When the composition according to the invention is a foam bath it preferably contains from 5 to 35% by weight of a detergent base containing more than 50% by weight of 2,3-dihydroxypropyl 2-(1-oxoalkyl)amino-2-deoxyglucopyranoside and from 65 to 95% by weight of an adjuvant.

The detergent base is generally chosen from compounds which are known to a person skilled in the art. Examples which may be mentioned are alkylamidobetaines such as cocoylamidopropylbetaine, ethoxylated sorbitan alkylcarboxylates such as ethoxylated sorbitan laurate end mixtures of these compounds.

The adjuvant is generally chosen from fatty acid mono- or triethanolamides (0–10% by weight), ethoxylated propylene glycol dialkylcarboxylates (0.5% by weight), polyethylene glycols such as triethylene glycol (0–5% by weight), alkyl acrylics such as oleylacrylic (0–5% by weight), vegetable oils such as sweet almond oil (0–10% by weight), sodium chloride, EDTA (0–5% by weight), fatty alcohols such as hexadecanol (0–2% by weight), preserving agents, perfumes, dyes, water and mixtures of these compounds.

When the composition according to the invention is a shower gel it preferably contains from 5 to 35% by weight of a detergent base containing at least 50% by weight of 2,3-dihydroxypropyl 2-(1-oxoalkyl)amino-2-deoxyglucopyranoside and from 65 to 95% by weight of an adjuvant.

The detergent base is generally chosen from polyoxyethylenated alkylsulphosuccinates such as cocoylsulphosuccinate containing 3 moles of ethylene oxide, N-alkylamidoglycinates, ammonium alkyl sulphates such as ammonium lauryl sulphate and mixtures of these compounds.

The adjuvant is generally chosen from ethoxylated propylene glycol alkyl carboxylates such as ethoxylated propylene glycol dioleate (0–5% by weight), alkylamidobetaines such as laurylamidopropylbetaine (0–5% by weight), pearlescent agents (0–7% by weight), acrylic gels (0–1% by weight), sodium chloride, complexing agents, preserving agents, perfumes, purified water and mixtures of these compounds.

Finally, the composition according to the invention may be a facial care formulation, especially an ointment, a cream or a beauty milk, which has a structure of gel type.

The examples which follow allow the invention to be illustrated without, however, limiting it.

In these examples the following methods of measurement are employed:

The foamability is measured by bubbling nitrogen at a constant rate (1 l/h) through a sinter (water permeability: 0.11 l/h) placed at the base of a graduated and thermostated test tube (32 mm×210 mm) containing 20 ml of an aqueous solution containing 3 g/l of 2,3-dihydroxypropyl 2-(1-oxoalkyl)amino-2-deoxyglucopyranoside and 12 g/l of glycerol. The quantity of foam generated by bubbling (1 minute and 40 seconds) is estimated volumetrically immediately after the bubbling is stopped. The volume of the foam thus formed is expressed in ml.

The wetting ability is measured according to the test which consists in monitoring during 600 seconds the quantity of solution to be tested (3 g of active substances per liter of glycerol; 25° C.) absorbed by an unbleached cotton fabric (2.5 cm×2 cm; 0.145 g; according to NF standard T73-406 (December 1975)). The piece of fabric skims over the surface of the solution of surfactants and the drag generated by the capillary rise of the solution is recorded continuously (automatic Kruss tension meter equipped with K 121 absorption software). The mass absorbed by the fabric when saturated (MS; in g) and the time needed to reach saturation (TS; in s) are measured.

The lowering of the surface tension of the water is measured by conventional tension measurement according to ISO Standard 304 modified in that the dimensions of the rectangular plate are 25 mm×5 mm×0.1 mm. The surface tension $\gamma$ is expressed in mN/m.

EXAMPLES

The examples which follow allow the invention to be illustrated without, however, limiting it.

Examples 1 to 6

To 21.57 g (0.10 mol) of glucosamine hydrochloride (G, 220-6; Aldrich), dissolved in 200 ml of an aqueous solution of sodium hydroxide (0.5N) at 20° C. are added, at a rate of 1 ml/min and with stirring (100 revolutions/min; shaft with a twin stirring blade) 20.3 g of acid chloride of the following acids: octanoic (Example 1; Aldrich Ref. 0,473-3), decanoic (Example 2; Aldrich Ref. 14,029-5), undecanoic (Example 3; Aldrich Ref. 24,943-2), undecylenic (Example 4; Aldrich Ref. 16,166-7), dodecanoic (Example 5; Aldrich Ref. 15,693-0) or tetradecanoic (Example 6; Aldrich Ref. 29,861-1) and, simultaneously, a 4N solution of sodium hydroxide, to fix and maintain the pH at 9.5. After 2 hours of additional stirring the pH is adjusted to 6 by addition of an aqueous solution of methanesulphonic acid in a concentration of 70% by weight. A precipitate forms, which is filtered off, drained, washed twice with 60 ml of water and again drained on a conventional sintered glass filter. The precipitate thus obtained is a mixture of the α and β anomers of the corresponding 2-(1-oxoalkylamino-2-deoxyglucopyranose, the yield of which, based on the dry material, is shown in Table 1.

10 g of the precipitate obtained above are brought into contact with 51.3 g (0.557 mol) of glycerol (13,487-2; Aldrich) and 0.48 g ($5 \times 10^{-3}$ mol) of methanesulphonic acid with stirring (300 revolutions/min) for 4 hours, at 110° C. and under a vacuum of 30 mm Hg.

The clear reaction mixture thus obtained is cooled to 40° C., diluted with 500 ml of absolute ethanol and the pH is adjusted to 6 by addition of powdered sodium hydrogencarbonate. The mixture obtained is filtered (sintered glass) and the filtrate is concentrated in a rotary evaporator (vacuum: 2.5 kPa; temperature: 60° C.). An oil is thus recovered which contains the α and β anomers of the corresponding 2,3-dihydroxypropyl 2-(1-oxoalkyl)amino-2-deoxyglycopyranoside (20% by weight in glycerol).

The oil obtained is analysed by thin layer chromatography (TLC) on a grafted silica plate (RP18; Merck) eluted with a 75:25 v:v MeOH/$H_2O$ mixture. The migration spots are developed with the aid of a solution of sulphuric acid in a concentration of 50% in water and heating to 120° C. for 2 minutes. A spot of elongate shape is observed whose Rf value is shown in Table 1.

The physicochemical characteristics of the abovementioned oil are shown in Table 1.

TABLE 1

| Example | Yield % | Rf | Foama-bility (ml) | Wetting ability MS (g) | Wetting ability TS (s) | Surface tension γ (mN/m) |
|---------|---------|------|------|-------|-----|------|
| 1 | 64.0 | 0.72 | 8 | 0.185 | 900 | 27.2 |
| 2 | 95.6 | 0.44 | 120 | 0.263 | 150 | 27.4 |
| 3 | 92.0 | 0.35 | 78 | 0.265 | 400 | 30.5 |
| 4 | 90.0 | 0.60 | 130 | 0.250 | 70 | 27.5 |
| 5 | 85.0 | 0.25 | 100 | 0.253 | 230 | 30.3 |
| 6 | 88.2 | 0.14 | 50 | 0.248 | 700 | 29.7 |
| Glycerol | — | — | — | — | — | — |
| APG* | — | — | 100 | — | — | — |

*Alkylpolyglucoside (Henkel Ref. APG 1200)

It is found that the foamability of the compounds of Examples 4, 2 and 5 is superior or equal to that of the APG, the reference product in this case.

It is seen that the foam formed during the measurement of the foamability is stable and that the decrease in the volume of the foam is more than 20% after 20 minutes (Examples 1 and 6).

The α and β anomers of the oil according to Example 4 are separated by flash chromatography (35–70 μm silica column, length: 25 cm; diameter: 5.6 cm; eluent: $CHCl_3$ then $CHCl_3$/MeOH, refractometry detection).

The α and β anomers thus obtained are characterized by the following analytical methods:

thin layer chromatography: identical Rf equal to 0.6 in the case of each anomer (silica plate; thickness: 200 μm; particle size: 5–10 μm; eluent 8:2 v:v $CHCl_3$/MeOH);

high performance liquid chromatography (HPLC): retention time ($T_R$) equal to 17.4 min and 14.7 min respectively (Lichrospher RP18 column; diameter: 4 mm; length 125 mm; particle size: 5 μm ; eluent: 50:50 v:v MeOH/$H_2O$; flow rate: 1 ml/min; detection: UV (λ: 220 nm) and differential refractometry;

IR spectroscopy (1% KBr disc: vOH: 3350 $cm^{-1}$; δ$CH_2$:2853 and 2825 $cm^{-1}$; vCO-$NH_2$:642 and 552 $cm^{-1}$;

$^{13}$C NMR 200 MHz: pyridine-$d_5$:

| | Chemical shift (ppm) |
|---|---|
| α anomer Carbon | |
| C1 | 99.22–99.02 |
| C2 | 55.48 |
| C3 | 71.71 |
| C4 | 74.31 |
| C5 | 82.31 |
| C6 | 70.55 |
| $(CH_2)_n$ | 36.59–33.95–29.58–29.26–29.04–26.24 |
| CO | 174.40 |
| C1' | 62.59–62.04 |
| C2' | 72.89–72.67 |
| C3' | 64.62–64.44 |
| —CH=$CH_2$ | 139.32 |
| —CH=$CH_2$ | 114.52 |
| β anomer: Carbon | |
| CO | 174.84 |
| C1 | 103.04 |
| C2 | 57.38 |

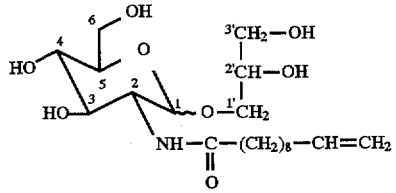

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:
1. A compound of formula:

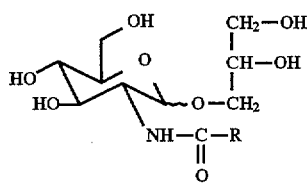

(I)

wherein R is a saturated or unsaturated, linear or branched alkyl group containing from 5 to 21 carbon atoms.

2. A compound according to claim 1, wherein R contains from 7 to 17 carbon atoms.

3. A process for the preparation of a compound according to claim 1, comprising:
   a) forming an N-acylglucosamine from glucosamine hydrochloride and $C_6$–$C_{22}$ acid chloride, and
   b) reacting the compound from step a) with glycerol in the presence of an acid catalyst.

4. A process according to claim 3, wherein the acid chloride/glucosamine hydrochloride molar ratio is between 0.7 and 1.3.

5. A process according to claim 3, wherein the ratio of the number of molar equivalents of glycerol to the number of molar equivalents of N-acylglucosamine from stage b) is between 1 and 50.

6. A process according to claim 3, wherein the catalyst is chosen from the group consisting of acids, resins in $H^+$ form and acidic clays.

7. A process according to claim 6, wherein the ratio of the number of molar equivalents of the acid to the number of molar equivalents of N-acylglucosamine is between $10^3$ and 1.

8. A process according to claim 6, wherein the quantity of resin or of clay, expressed as weight equivalent calculated on the basis of 1 molar equivalent of N-acylglucosamine, is between 0.05 and 6.

9. A detergent composition comprising from 0.1 to 60% by weight of a compound according to claim 1, and from 40 to 99.9% by weight of a detergent base and/or of an adjuvant.

10. A cosmetic composition comprising from 0.1 to 50% by weight of a compound according to claim 1, and from 50 to 99.9% by weight of an excipient and/or of a detergent base and/or of an adjuvant.

11. A cosmetic composition according to claim 10, wherein the cosmetic is selected from the group consisting of mild liquid soaps, shampoos, foam baths, shower gels and facial care formulations.

12. A method of providing a surface-active property to a composition, comprising including in the composition an effective mount of a surface-active-effective compound according to claim 1.

13. A method of providing a detergent property to a composition, comprising including in the composition an effective amount of a detergent-effective compound according to claim 1.

14. A method of providing an antidandruff property to a composition, comprising including the composition an effective amount of an antidandruff-effective compound according to claim 1.

15. A method of providing a hair-conditioning property to a composition, comprising including the composition an effective amount of a hair-conditioning-effective compound according to claim 1.

16. A cosmetic composition of claim 11, wherein the composition is a facial care formulation and is an ointment, cream or beauty milk.

* * * * *